United States Patent [19]

Goebel

[11] 4,274,000
[45] Jun. 16, 1981

[54] X-RAY POWDER DIFFRACTOMETER

[75] Inventor: Herbert Goebel, Munich, Fed. Rep. of Germany

[73] Assignee: Siemens Aktiengesellschaft, Berlin & Munich, Fed. Rep. of Germany

[21] Appl. No.: 112,463

[22] Filed: Jan. 16, 1980

[30] Foreign Application Priority Data

Feb. 23, 1979 [DE] Fed. Rep. of Germany ....... 2907160

[51] Int. Cl.$^3$ ............................................ G01N 23/20
[52] U.S. Cl. ............................ 250/272; 250/277 CH; 250/280
[58] Field of Search ............... 250/272, 274, 273, 278, 250/280, 277 R, 277 CH

[56] References Cited

U.S. PATENT DOCUMENTS

| 3,576,993 | 5/1969 | Hagg | 250/278 |
| 4,144,450 | 3/1979 | Goebel | 250/272 |

OTHER PUBLICATIONS

"Grundlagen und Anwendung der Röntgenfeinstrukturanalyse", Oldenburg, Verlag, 1959, pp. 160-171.

Primary Examiner—Alfred E. Smith
Assistant Examiner—Carolyn E. Fields
Attorney, Agent, or Firm—Hill, Van Santen, Steadman, Chiara & Simpson

[57] ABSTRACT

An X-ray powder diffractometer functioning as a goniometer is disclosed wherein a monochromatic X-ray source is provided together with a sample to be analyzed and a detector means with position sensitive behavior. A transport system for digitally controllable advance drive is provided so as to advance the detector along an arc suited for a Guinier method for transmission and/or back reflection beam direction. An electronic analysis system is provided for preparing an intensity diagram of a local distribution of diffracted radiation for a given position location $2\theta$ of the detector. The analysis system includes an amplifier/discriminator for delivering a time signal corresponding to the position/location of a respective single photon event received from the detector. A time-digital converter connected to the amplifier/discriminator is also provided together with a multichannel analyzer connected to the time-to-digital converter by a digital adder. The position-sensitive detector is located diametrically opposite the sample on the Guinier circle so as to form an assembly. This assembly is rotated in the primary beam such that the primary beam always impinges on the sample, and the detector is always in a focus of the diffracted radiation.

5 Claims, 5 Drawing Figures

X-RAY POWDER DIFFRACTOMETER

BACKGROUND OF THE INVENTION

The invention relates to X-ray powder diffractometers having a monochromatic X-ray source; a detector with position or location sensitive behavior; a mechanism with digitally controllable advance drive for an advance of the detector along an arc suited for the Guinier Method for transmission and/or back reflection beam geometry; and an electronic analysis system for preparing an intensity diagram of the intensity distribution of the diffracted radiation along the diffraction angle 2 Theta. The main components are an amplifier/discriminator module which delivers a time signal corresponding to the position-location of the respective elementary event in the detector, a time-digital converter, a digital adding module, and a multichannel analyzer.

In X-ray powder diffractometry the Guinier Method is one of the most widespread diffraction measuring techniques. Further details regarding the Guinier Principle can be learned from the book of H. Neff "Grundlagen und Anwendung der Röntgenfeinstrukturanalyse", Oldenburg-Publisher, 1959, particularly pages 160 through 171, incorporated herein by reference. The Guinier Method uses a monochromatic X-ray beam, such as copper $K\alpha_1$ radiation, and a precise focusing arrangement consisting of a monochromator, sample and detector. The Guinier Method is suitable for plots in the entire interference angular range. Due to the use of strictly monochromatic radiation very low background diffraction patterns are obtained, whereby the detection of very weak interferences is possible which will be lost in normal techniques.

However, a disadvantage of this method is the relatively long measuring time since the primary monochromator supplies only a low beam yield for the measurement.

An increase in the measuring speed can be achieved by a more sensitive detection system, a position sensitive X-ray detector. In existing systems either photographic films or non-position-sensitive X-ray detectors, such as scintillation counters, in conjunction with a fine measuring slit rotating along the Guinier focusing circle have been employed to monitor the diffracted radiation distribution.

In U.S. Pat. No. 4,144,450, incorporated herein as reference, an automatically controlled powder diffractometer is described which, by means of a linear position sensitive proportional counter tube, can increase its slewing speed by about 2 orders of magnitude so that the scanning times can be reduced to less than five minutes. It is here provided that the detector is continuously nonintermittently moved i.e. there is no relevant step movement of the advance along the measuring arc noticeable. In addition, a software system is employed to analyze and interpret the powder diagram.

SUMMARY OF THE INVENTION

The present patent application relates to a variant of the X-ray diffractometer described in U.S. Pat. No. 4,144,450 and has the purpose to solve the problem in using the Guinier technique, and takes into account that in the case of the employed position sensitive X-ray detector in the form of a proportional counter tube, a good position resolution can only be obtained if a vertical (or nearly vertical) incidence of the X-rays on the counter tube axis is provided.

This object is solved with an X-ray diffractometer of the invention wherein the position sensitive detector is arranged diametrically opposite the sample on the Guinier circle and that this arrangement is rotated in the primary beam in such a fashion that the latter always impinges the sample and the detector is always in the focus of the diffracted radiation due to the Guinier focussing construction.

Through the application of the Guinier Principle in combination with the position-sensitive detector in the case of an X-ray powder diffractometer, a high resolution and angulur accuracy, above all for low diffraction angles (low indexed lattice planes), as well as a low background can be obtained. With application of the inventive arrangement the measuring times are less than five minutes for a diffraction diagram of average samples over an anguler range of $5° \leq 2\theta \leq 80°$ using a conventional 1 to 1.5 kW fine focus X-ray tube as primary beam source.

DESCRIPTION OF THE PREFERRED EMBODIMENTS

Figure 1:
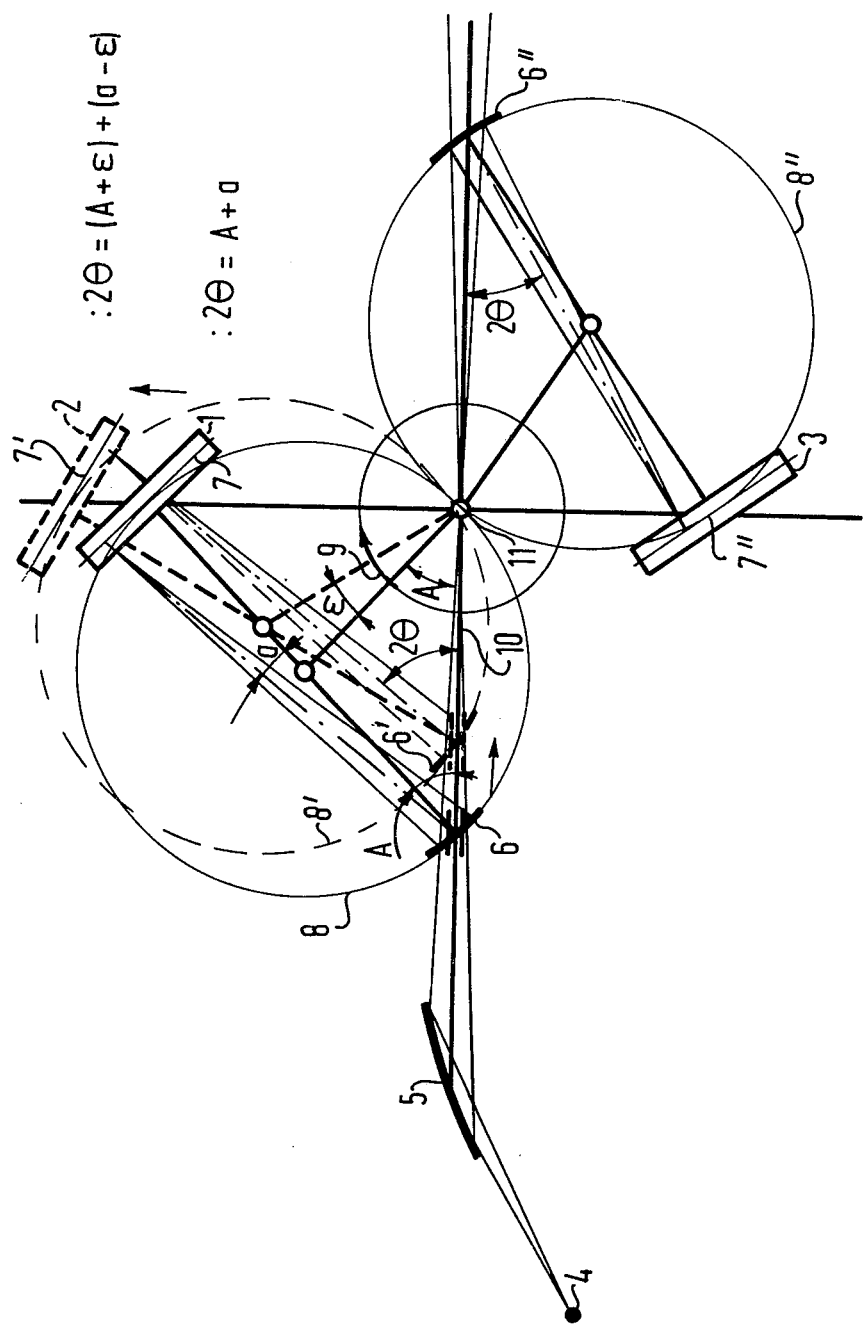
FIG. 1 shows a basic drawing of the inventive arrangement with two different sample positions.

In FIG. 1 the employed Guinier System is shown in principle for transmission (position 1 and 2) as well as for back reflection beam geometry (position 3). The radiation emitted by an X-ray source 4 is focused on a so-called Johansson-Monochromator 5 consisting of a curved and grinded germanium crystal orientated in a (111)-direction. This radiation impinges on the sample 6 which is movable in a direction of the primary beam 10. The sample 6 consists of an $\alpha$-quartz powder in the present sample embodiment. As can be learned from FIG. 1, in the respective position (1, 2, 3), sample 6 (6', 6'') and detector 7 (7', 7'') are fixed on the Guinier circle 8 (', 8'') diametrically opposite of one another. In this way the diffracted X-ray beam from the sample 6 (6', 6'') enters prependicularly into the detector 7 (7',7'') which additionally is in the focus of the diffracted radiation. Through the arrow 9 the goniometer drive for the angular range $2\theta$ is marked. In position 1, $2\theta$ corresponds to the sum of the angles A+a; in position 2, to the sum of $(A+\epsilon) +(a-\epsilon)=A+a$. In other words, the digitized angular value of this movement is combined with the digital address of the incidence position of the X-ray quantum in the position sensitive detector such that the resulting address registered in a multichannel counter of 4 K×20 bits becomes independent of the movement. A diffraction maximum is therefore accumulated into the same channels of the multichannel counter as long as the detector travels across this reflection. In the angular range of $2\theta = 90°$ the beam hits the sample only as a tangent. However, since the detector simultaneously detects an angular range of ±5°, the intensities are here also determined with sufficient yield.

With the same arrangement as in FIG. 1, the measurement in reflection (Guinier-backscatter-technique) is also possible (position 3). Angles of $90° \leq 2\theta < 180°$ are here detected. The sample is referenced 6''; the position sensitive detector 7''; and the measuring circle 8''.

The static point of the arrangement is the primary beam focus 11 disposed on the primary beam 10 which (primary beam focus 11) must be the center of the goniometer drive and hence determines the position of the driving axle.

Figure 2:
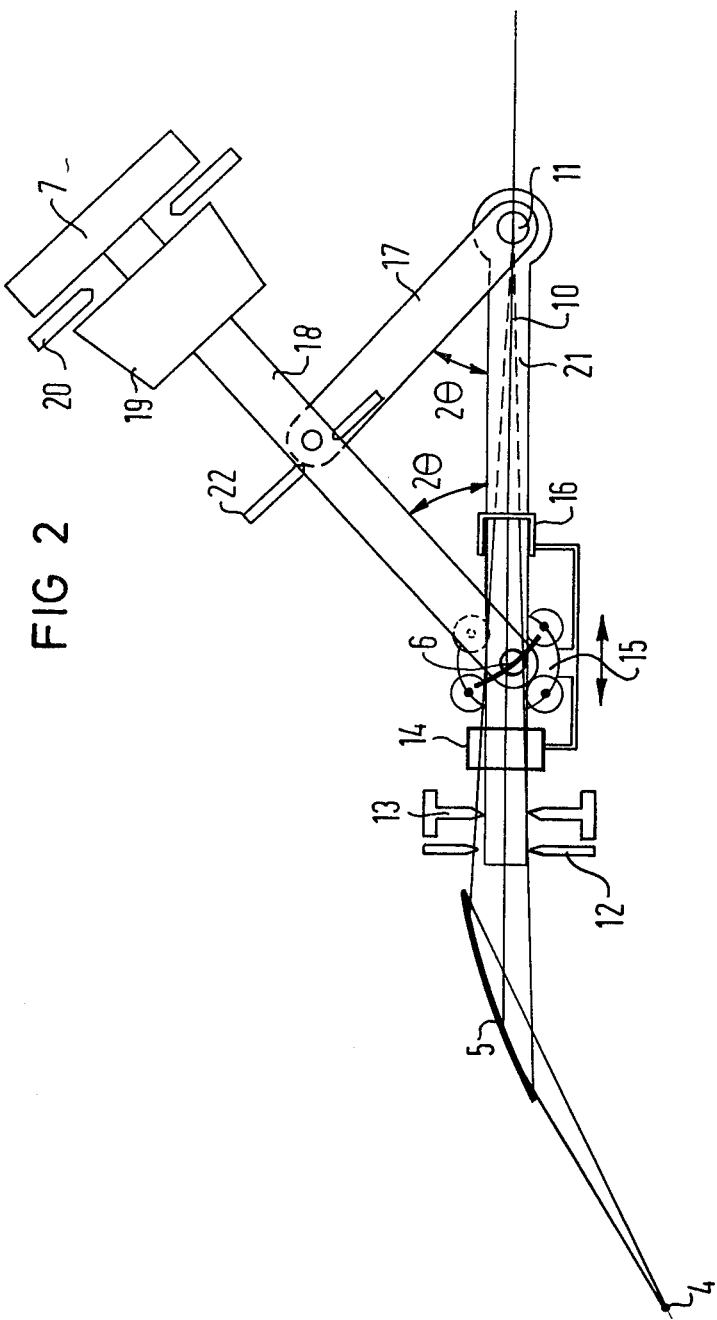
FIG. 2 shows a step motor arrangement with rods for verifying the movement of the sample and the detector to satisfy the Guinier focussing conditions.
Figure 3:
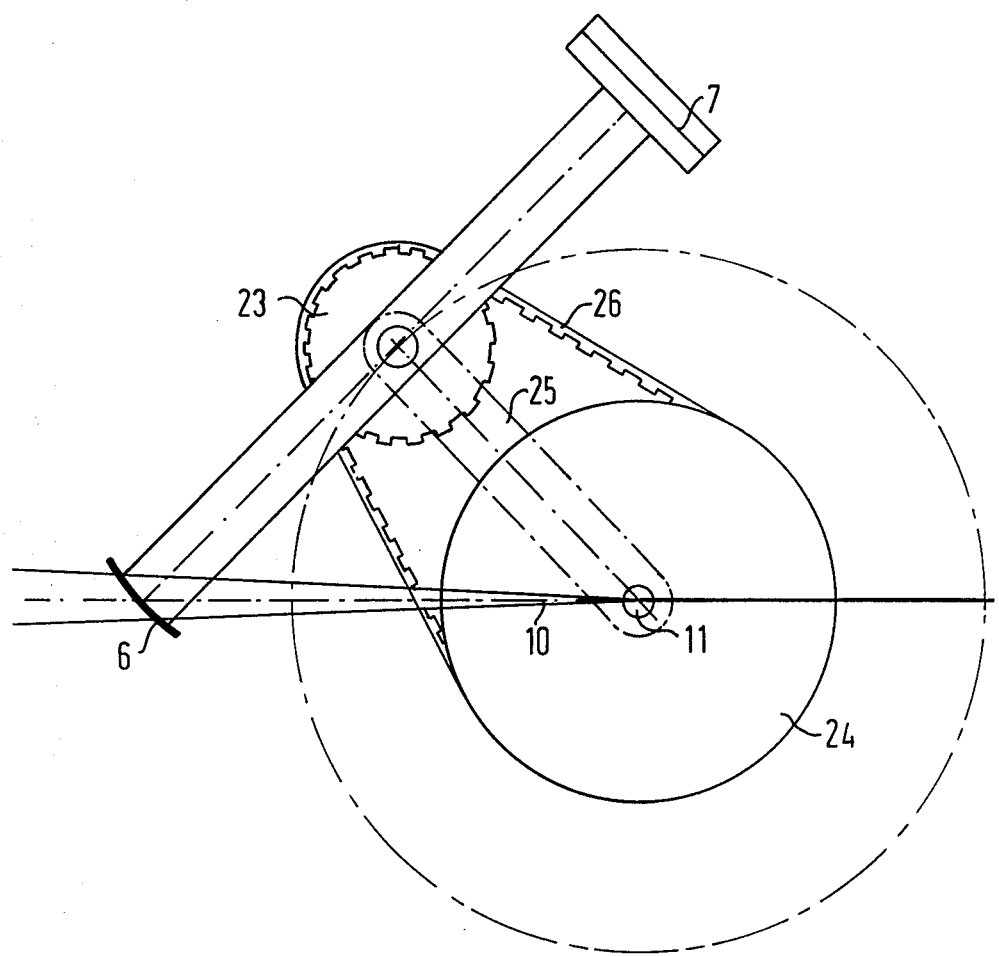
FIG. 3 shows a similar arrangement in which the same movement is achieved by using a 2:1 gear with a toothed belt.
Figure 4:
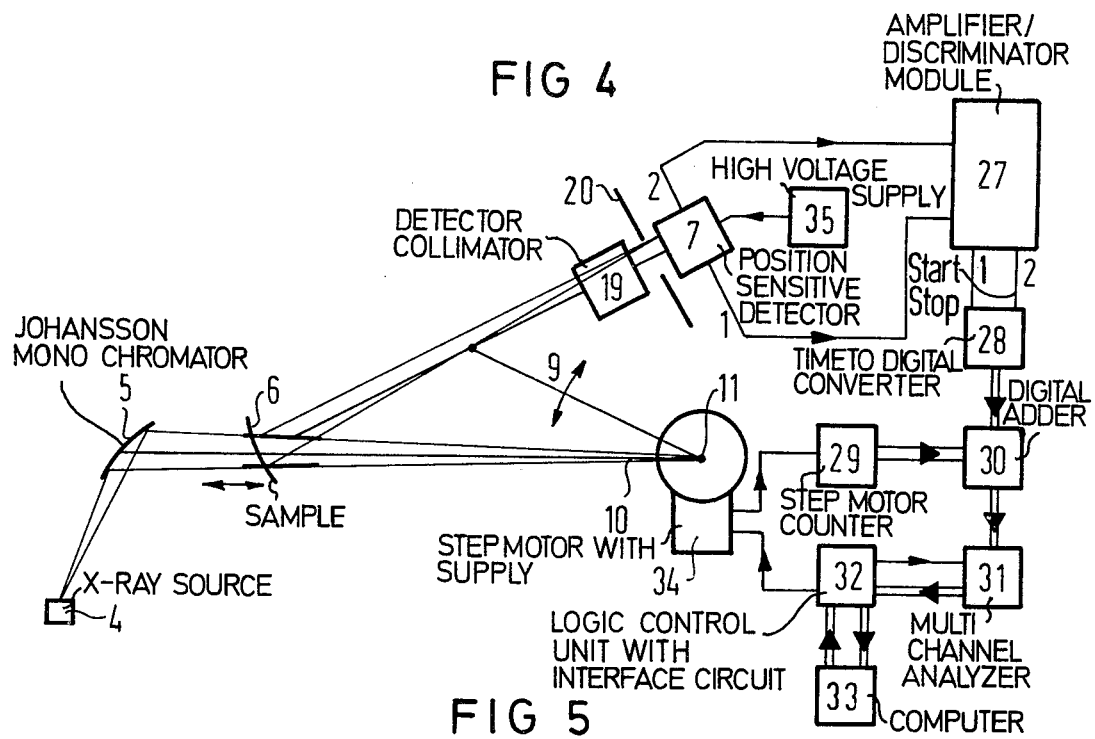
FIG. 4 shows a block circuit diagram for the electronic analysis system.
Figure 5:
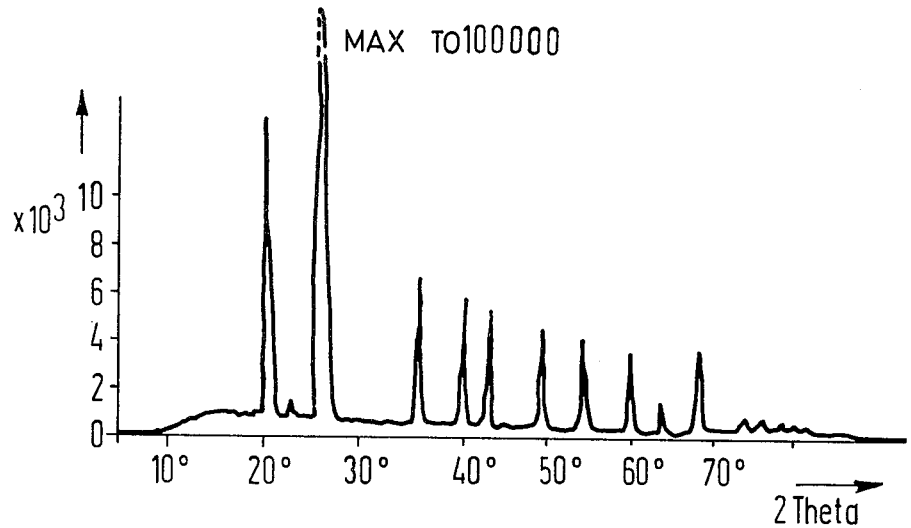
FIG. 5 shows a diffraction diagram utilizing $\alpha$-quartz powder as a sample with copper $K\alpha_1$- radiation, and which was recorded in one minute.

With the preferred embodiment of the invention, a transport system as shown in FIGS. 2 and 3 is provided for digitally controllable advance drive in accordance with the circuitry shown in FIG. 4. The detector is advanced along the arc suited for the Guinier method for transmission and/or back reflection beam direction. The electronic analysis system shown in FIG. 4 is provided for preparing an intensity diagram such as shown in FIG. 5 of a local distribution of diffracted radiation for given position locations $2\theta$ of the detector. The analysis system of FIG. 4 includes an amplifier/discriminator module 27 for delivering a time signal corresponding to the position/location of a respective single photon event received from the detector 7. A time-digital converter 28 connected to the amplifier/discriminator module 27 is also provided together with a multichannel analyzer 31 connected to the time-to-digital converter 28 by a digital adder 30. The position-sensitive detector 7 is located diametrically opposite the sample 6 on the Guinier circle so as to form an assembly. This assembly is rotated in the primary beam such that the primary beam always impinges on the sample, and the detector is always in a focus of the diffracted radiation.

FIG. 2 illustrates a sample embodiment in a transmission range $-80° \leq 2\theta \leq 80°$ in which the movement of the sample 6 is verified by a single circuit-step motor drive which is centered on the primary beam focus. In addition to the reference numbers already mentioned in the description of FIG. 1, the following reference numerals apply:

12 = primary beam diaphragm
13 = Zero beam adjustment
14 = Primary beam collimator (nominal slits)
15 = Slide for the sample (mounted without tolerance)
16 = Primary beam catcher
17 = Driving arm
18 = Sample/detector arm
19 = Detector collimator (nominal slits)
20 = Detector-side range diaphragm
21 = Rail in zero beam direction
22 = Pre-diaphragm The drive mechanism shown in FIG. 2 includes an arm 18 between the sample and detector, a drive arm 17 with one end pivotally connected to the sample/detector arm 18 and the other end connected for rotation by the step motor drive, a bar 21 arranged along a zero beam direction of the goniometer, and a slide 15 which slides along the bar 21 and has a pivot for rotation of the sample. The sample/detector arm 18 has one end connected to the pivot.

By rotating the goniometer axis around point 11 (primary dot or point = rotational point of the step motor drive 17 for $2\theta$ (800 steps per degree)) the movement of the sample 6 along the primary beam 10 and the rotation of the sample-detector arm 18 by the angle $2\theta$ in linear form results. The linear position information from the position-sensitive detector 7 can thereby be linked, by simple addition, with the rotation angle $2\theta$.

In FIG. 3, another type of drive for sample 6 and position-sensitive detector 7 on the Guinier measuring circle by means of a 1:2-toothed belt drive is illustrated. Two driving pulleys 23 and 24, of which the larger pulley 24 is fixed in the goniometer axis 11, are connected with the driving arm 25 via a toothed belt 26. The transmission and reflection takes place in the angular range $-170° \leq 2\theta \leq 170°$.

FIG. 4 illustrates a sample embodiment of an inventive X-ray powder diffractometer with an electronic analysis system. The same reference numerals as in FIG. 1 or 2 also apply here. In addition, 27 denotes the amplifier/discriminator module delivering the time signal corresponding to the position-location of the respective event in the position-sensitive detector. Module 27 and the building blocks for the system are commercially available units:

| | |
|---|---|
| amplifier-discriminator module 27 | Siemens AG, E 689 |
| the time-digital converter 28 | Siemens AG, E 689 |
| the step motor counter divider 29 | Siemens AG, E 689 |
| the digital or binary adder 30 | Siemens AG, E 689 |
| the multichannel analyzer or counter 31 | Canberra Ltd. |
| the logic control unit with interface circuit 32 | Siemens AG, E 689 |
| the computer 33 | Digital Equipment Corp. |
| the step-motor with supply 34 | Siemens AG, E 689 |
| the high voltage supply for the detector 35 | Siemens AG, E 689 |
| position sensitive detector 7 | Siemens AG, E 689 |
| step motor drive 17 | Huber Diffraktionstechnik, Rimsting W. Germany |

FIG. illustrates a diffraction diagram of α-quartz powder which was recorded with the electronic analysis system shown in FIG. 4 in one minute. The digitization here amounts 0.05° per channel. The x-radiation employed consisted of copper-$K\alpha_1$ radiation.

The abscissa of the diagram provides the $2\theta$ scale in angular degrees. On the oridnate the intensity = pulses per channel is plotted. Due to their angular position and intensity, the maxima occurring are characteristic of the examined material and its lattice unit cell. The diagram is intended to illustrate, in particular, the high peak/background ratio as well as the line shape of the pure $K\alpha_1$ reflections.

The diffractometer of the invention operates with a rotational speed, or angular velocity, respectively, of up to 400°/min. This corresponds to a plotting time for the angular range of interest of $5° \leq 2\theta \leq 80°$ of approximately 10 seconds.

The technological advance as compared with the method described in U.S. Pat. No. 4,144,450 is in the advantages which the Guinier geometry offers in relation to the Bragg-Brentano Geometry:

1. measurements which have very low background interference, thereby shortening measuring time and lowering detector load;
2. pure $K\alpha_1$-diffractograms;
3. high accuracy, particularly in the case of small diffraction angles due to the precise beam geometry; also zero point errors (i.e., the precise position of the primary beam) can be avoided since to the left and right of the zero beam, identical reflections can be measured and the precise zero point of the 2θ scale is capable of being determined therefrom by way of computation;

4. small sample quantity;

5. the diagrams are obtained in times which are comparable to the methods described in the U.S. Pat. 4,144,450; however, they frequently achieve a better peak/background ratio than the best Bragg-Brentano diffractometers equipped with a secondary monochromator, which, however, then operate approximately 100 times more slowly; and 6. the diffracted radiation always selects the shortest path (perpendicular) from its origin to the detector; this additionally contributes to background reduction, particularly in the case of oblique incidence of the primary beam.

Although various minor modifications may be suggested by those versed in the art, it should be understood that I wish to embody within the scope of the patent warranted hereon, all such embodiments as reasonably and properly come within the scope of my contribution to the art.

I claim as my invention:

1. An X-ray powder diffractometer functioning as a goniometer, comprising: a monochromatic X-ray source; a sample; a detector means for position sensitive behavior; transport means for digitally controllable advance drive for advance of the detector means along an arc suited for a Guinier Method for transmission and/or back reflection beam direction; analysis means for preparing an intensity diagram of a local distribution of diffracted radiation for a given position location 2θ of the detector means; said analysis means including an amplifier/discriminator means for delivering a time signal corresponding to the position-location of a respective primary event received from the detector means, a time-to-digital converter connected to the amplifier/discriminator means, a multichannel analyzer connected to the time-to-digital converter by a digital adder; the position sensitive detector means being located diametrically opposite the sample on a Guinier circle so as to form an assembly; and the assembly being positioned and rotated in the primary beam such that the primary beam always impinges on the sample and the detector is always in a focus of the diffracted radiation.

2. A diffractometer according to claim 1 wherein in order to move the sample and position-sensitive detector means assembly on the Guinier circle, a step motor drive is provided which is centered at an axis of the goniometer at a beam focus of an X-ray beam from the X-ray source, an arm being provided between the sample and detector means, a drive arm having one end pivotably connected to the sample-detector means arm and its other end connected for rotation by the step motor drive, a bar arranged along a zero beam direction of the goniometer, slide means arranged to slide along the bar and said slide means having a pivot means for rotation of the sample, and the sample-detector means arm having one end connected to the pivot means, whereby the sample-detector means assembly is rotated through an angle 2θ of the goniometer.

3. A diffractometer according to claim 1 wherein the detector means-sample assembly comprises an arm between the detector means and sample, a drive pulley connected to the arm for rotation thereof, and a second drive pulley connected to the arm drive pulley by flexible drive means so as to cause rotation of the assembly when the second drive pulley is rotated.

4. A diffractometer according to claim 1 wherein a high-resolution impulse provided is employed for digital registration of goniometer angle 2θ wherein 2θ corresponds to an angle between an axis of the primary beam and an axis on which the sample and detector means are centered.

5. An X-ray powder diffractometer functioning as a goniometer, comprising: an X-ray source; a sample; a detector means for position sensitive behavior; transport means for advance of the detector means along an arc suited for a Guinier Method for transmission and/or back reflection beam direction and which has a Guinier circle associated therewith; analysis means for preparing an intensity diagram of a local distribution of diffracted radiation for a given position location 2θ of the detector means; the position sensitive detector means being located diametrically opposite the sample on the Guinier circle so as to form an assembly; and the assembly being positioned and rotated in the primary beam such that the primary beam always impinges on the sample and the detector is always in a focus of the diffracted radiation.

* * * * *